United States Patent
Mehendale et al.

(10) Patent No.: US 11,925,453 B2
(45) Date of Patent: Mar. 12, 2024

(54) VIRTUALLY-ORIENTED ELECTROMAGNETIC TRACKING SYSTEM FOR MEDICAL INSTRUMENT NAVIGATION

(71) Applicant: KONINKLIJKE PHILIPS N.V., Eindhoven (NL)

(72) Inventors: Aditya Mehendale, Geldrop (NL); Funda Sahin, Eindhoven (NL); Gregory Cole, Ossining, NY (US); Hao Su, Hartsdale, NY (US); Vijay Parthasarathy, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 270 days.

(21) Appl. No.: 17/222,389

(22) Filed: Apr. 5, 2021

(65) Prior Publication Data

US 2021/0219865 A1 Jul. 22, 2021

Related U.S. Application Data

(62) Division of application No. 15/529,766, filed as application No. PCT/IB2015/058726 on Nov. 12, 2015, now Pat. No. 10,966,629.

(60) Provisional application No. 62/085,685, filed on Dec. 1, 2014.

(51) Int. Cl.
*A61B 5/06* (2006.01)
*A61B 1/267* (2006.01)
(Continued)

(52) U.S. Cl.
CPC ............ *A61B 5/062* (2013.01); *A61B 1/2676* (2013.01); *A61B 5/425* (2013.01);
(Continued)

(58) Field of Classification Search
CPC .... A61B 5/062; A61B 34/20; A61M 25/0127; A61M 25/09
See application file for complete search history.

(56) References Cited

U.S. PATENT DOCUMENTS

| 3,805,768 A | 4/1974 | Barefoot |
| 3,871,359 A * | 3/1975 | Pacela ...................... A61B 5/25 324/692 |

(Continued)

FOREIGN PATENT DOCUMENTS

| EP | 2335553 A1 | 6/2011 |
| JP | 2003019104 A | 1/2003 |

(Continued)

*Primary Examiner* — Angela M Hoffa
*Assistant Examiner* — Younhee Choi

(57) ABSTRACT

A medical device for the electromagnetic tracking of a medical instrument transported through the medical device. The medical device has a central axis and a channel that receives and transports a medical instrument through the medical device. The channel extends to a distal portion of the medical device and connects with an opening in the medical device that is not aligned with the central axis. The medical device includes a tracking component that is a plurality of coordinated electromagnetic sensors for generating a virtual axis of travel for the medical instrument, with the virtual axis passing through the opening of the device and being aligned with tool insertion axis.

15 Claims, 10 Drawing Sheets

(51) Int. Cl.
*A61B 5/00* (2006.01)
*A61B 17/00* (2006.01)
*A61B 34/20* (2016.01)
*A61M 25/01* (2006.01)
*A61M 25/09* (2006.01)
*A61B 34/30* (2016.01)

(52) U.S. Cl.
CPC ........ *A61B 17/00234* (2013.01); *A61B 34/20* (2016.02); *A61M 25/0127* (2013.01); *A61M 25/09* (2013.01); *A61B 2017/00274* (2013.01); *A61B 2034/2051* (2016.02); *A61B 2034/2061* (2016.02); *A61B 2034/301* (2016.02)

(56) References Cited

U.S. PATENT DOCUMENTS

| | | | | |
|---|---|---|---|---|
| 5,443,077 | A * | 8/1995 | Krogh | .................... A61B 5/062 128/897 |
| 6,374,667 | B1 | 4/2002 | Eriksen | |
| 8,454,497 | B2 | 6/2013 | Tanaka | |
| 9,138,165 | B2 | 9/2015 | Holsing | |
| 2008/0097475 | A1 | 4/2008 | Jaggi | |
| 2009/0062739 | A1 | 3/2009 | Anderson | |
| 2010/0234724 | A1 * | 9/2010 | Jacobsen | ................ A61B 34/20 600/424 |
| 2010/0301841 | A1 | 12/2010 | Anderson | |
| 2010/0305427 | A1 | 12/2010 | Huber | |
| 2012/0130228 | A1 * | 5/2012 | Zellers | ................... A61B 5/062 600/424 |
| 2013/0023353 | A1 | 1/2013 | Wright | |
| 2013/0223702 | A1 | 8/2013 | Holsing | |
| 2013/0303945 | A1 | 11/2013 | Blumenkranz | |
| 2015/0173643 | A1 | 6/2015 | Govari | |

FOREIGN PATENT DOCUMENTS

| | | |
|---|---|---|
| JP | 2009131406 A | 6/2009 |
| WO | 2008088488 A1 | 7/2008 |
| WO | 2012098551 A1 | 7/2012 |
| WO | 2013031637 A1 | 3/2013 |

* cited by examiner

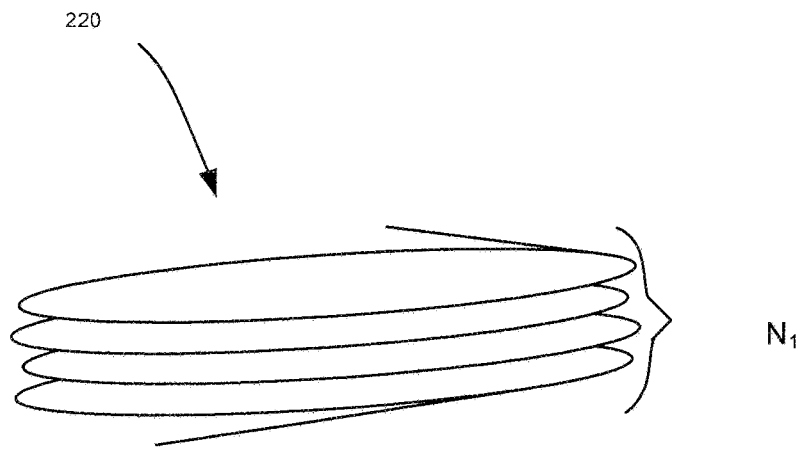
FIG. 2B
FIG. 2C
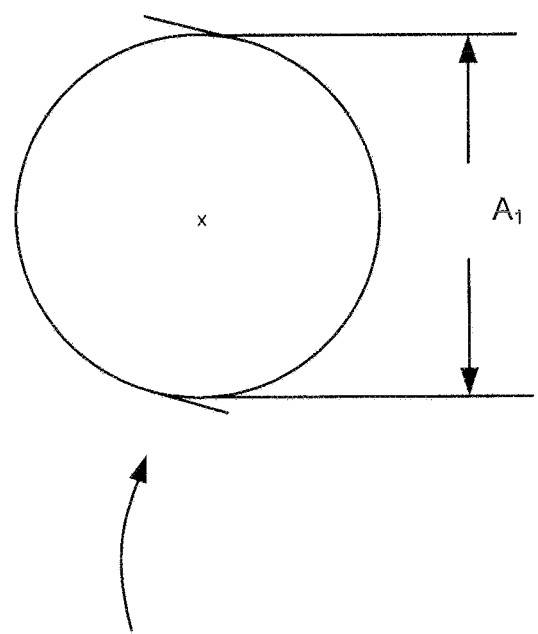

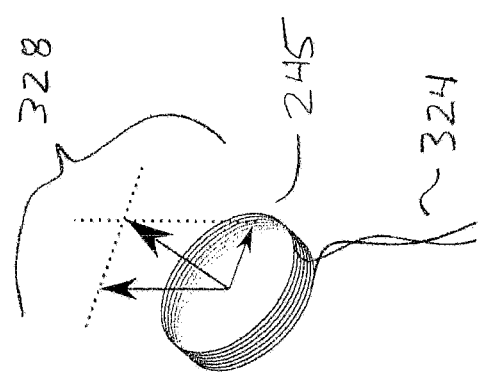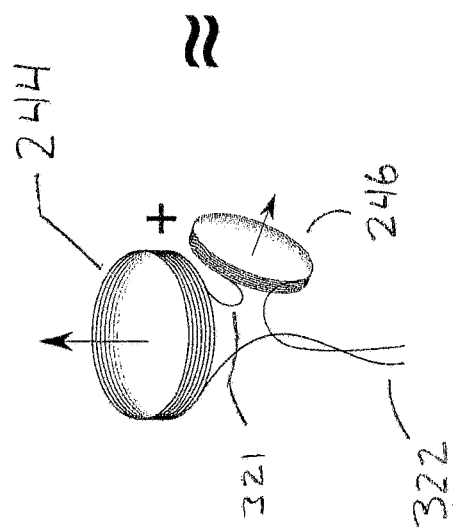
FIG. 6

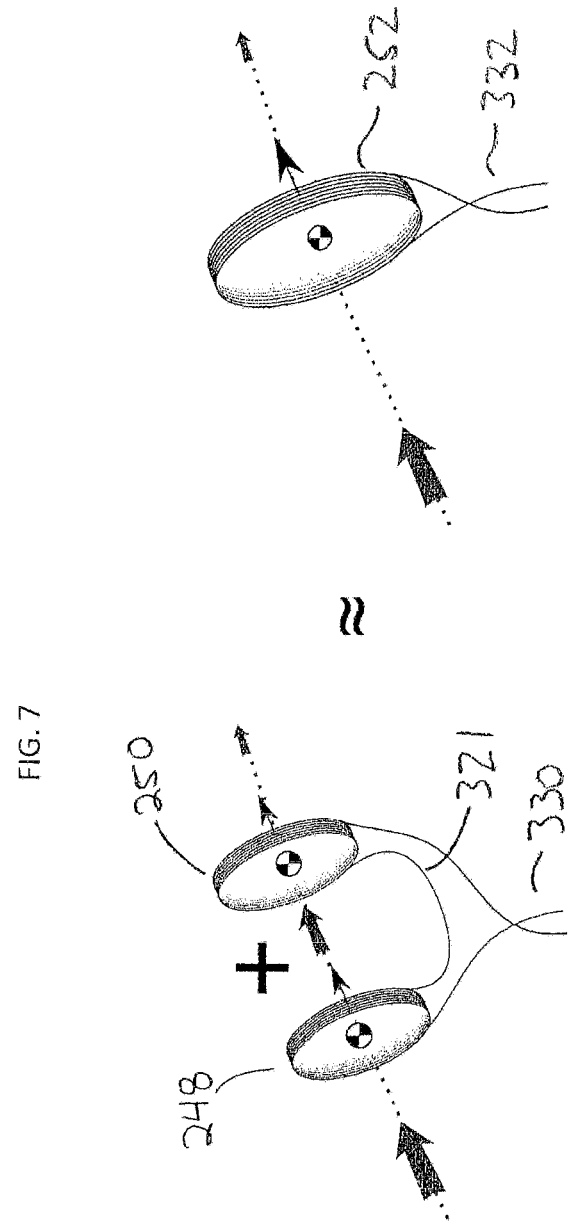

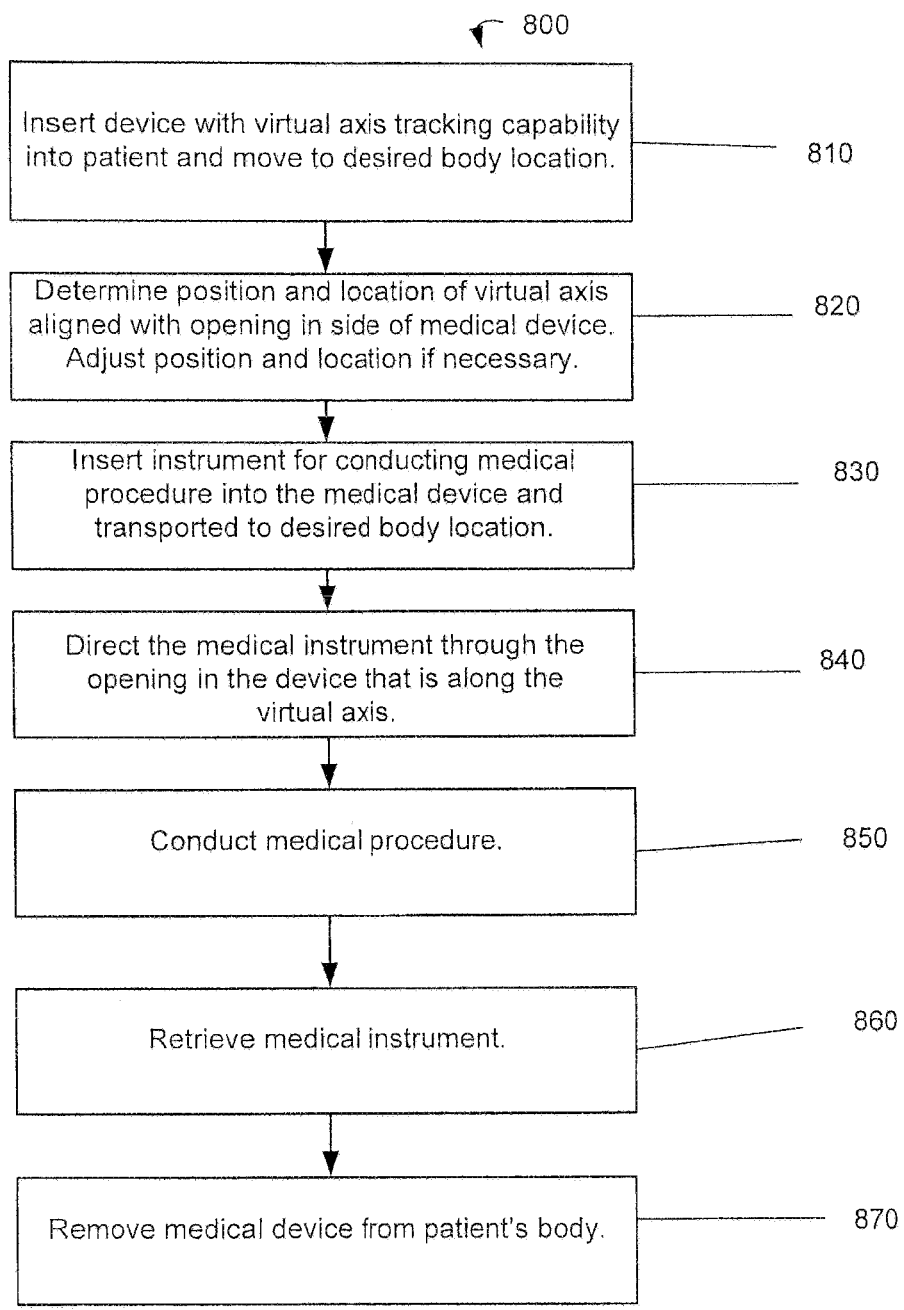

VIRTUALLY-ORIENTED ELECTROMAGNETIC TRACKING SYSTEM FOR MEDICAL INSTRUMENT NAVIGATION

RELATED APPLICATION INFORMATION

This application is a Divisional Application under 35 U.S.C. § 121 of U.S. application Ser. No. 15/529,766 filed on May 25, 2017, which is the U.S. National Phase application under 35 U.S.C. § 371 of International Application Serial No. PCT/IB2015/058726, filed on Nov. 12, 2015, which claims the benefit of U.S. Application Ser. No. 62/085,685, filed on Dec. 1, 2014. Each of these applications are hereby incorporated by reference herein in their entirety.

BACKGROUND

Technical Field

The present disclosure relates to medical devices and systems, in particular, to navigation and tracking of invasive medical devices. Even more particularly, the present disclosure relates to medical instruments and more particularly to a system and method to electromagnetically track a component with electromagnetic sensors.

Description of the Related Art

In-body tracking of invasive medical devices to determine the spatial relation and distance between the instrument and anatomical structures is employed in performing safe and precise invasive procedures. Devices such as endoscopes, catheters, guidewires etc., navigate through human body passages such as vasculature, gastrointestinal (GI) tracts, lung airways, and others. While these passages provide a pathway for navigation, in many cases they have small diameters, requiring the design of instruments with small diameters/cross sectional profiles. In addition, often there is a need to exit the lumen laterally such as in the case of vessel re-entry, or air bronchus negative lesions in peripheral lung navigation.

A biopsy device is exemplary of an interventional instrument. A biopsy device is used to take a biopsy sample, drawn through a procedure in which a sample of tissue is obtained for ex vivo pathologic analysis. A biopsy device includes a biopsy needle for acquiring a tissue sample and a lumen provided through a cannula. The needle could be attached to a guide wire threaded through the lumen. The guide wire and needle can be fired through the device and into the patient's body with actuation, such as by a firing handle provided on the device.

Among the state of the art proposals for tracking a catheter tip, there are 6-degree of freedom (6-DOF) electromagnetic tracking sensors and 5-degree of freedom (5-DOF) electromagnetic tracking sensors. These sensors, which are affixed to the tip, have shortcomings with regard to tracking a device with a lateral opening through which a medical instrument will be deployed. A 6-DOF sensor is a pair of electromagnetic coils that are large relative to the diameter of the sampling tool, thereby presenting a design problem. A device having a 5-DOF cannot track the tool insertion angle due to a lack of roll tracking, and thus cannot effectively target a site of interest, for example, a lesion, that lies outside the body passageway that the device travels through and therefore lies away from the central axis of the device.

There is a need for an electromagnetic sensor arrangement that provides a high degree of tracking accuracy for a medical device that can be deployed laterally, which arrangement fits within the existing design constraints, and which is relatively inexpensive to manufacture.

SUMMARY

In accordance with the present principles, described herein is a medical device having a central axis, a channel that receives and transports a medical instrument through the medical device, the channel extending to a distal portion of the medical device and being in communication with an opening in the medical device that is not aligned with the central axis, the opening being aligned with a tool insertion axis, and a tracking component that is a plurality of coordinated electromagnetic sensors for generating a virtual axis of travel for the medical instrument through the opening, the virtual axis passing through the opening of the device and being aligned with the tool insertion axis.

In one embodiment, the medical device has a distal portion provided with an opening positioned lateral to the central axis of the device to allow for a tool or instrument to be deployed laterally, e.g., lateral to the central axis of the device. The device includes electromagnetic sensors in the form of a plurality of wound coils of an electromagnetic material that are positioned relative to each other in a manner described herein, which provides for tracking along a virtual axis of instrument deployment. The virtual axis, which passes through the opening positioned in a side of the device, is not aligned with the central axis of the device, e.g., the longitudinal direction of the device. In one embodiment, the virtual axis and the central device axis intersect with each other at an angle such as an oblique angle.

In accordance with present principles, further described are a system and method that employ the medical device.

BRIEF DESCRIPTION OF DRAWINGS

This disclosure will present in detail the following description of preferred embodiments with reference to the following figures wherein:

FIG. 2B is a perspective view of an aspect of an embodiment in accordance with present principles;

FIG. 2C is a top plan view of an aspect of an embodiment in accordance with present principles;

FIG. 6 depicts a combination coil and a single pickup-coil;

FIG. 7 depicts a single pickup-coil and summed multiple parallel coils;

FIG. 9 is a method for tracking a medical device embodying present principles.

DETAILED DESCRIPTION OF EMBODIMENTS

Figure 1:
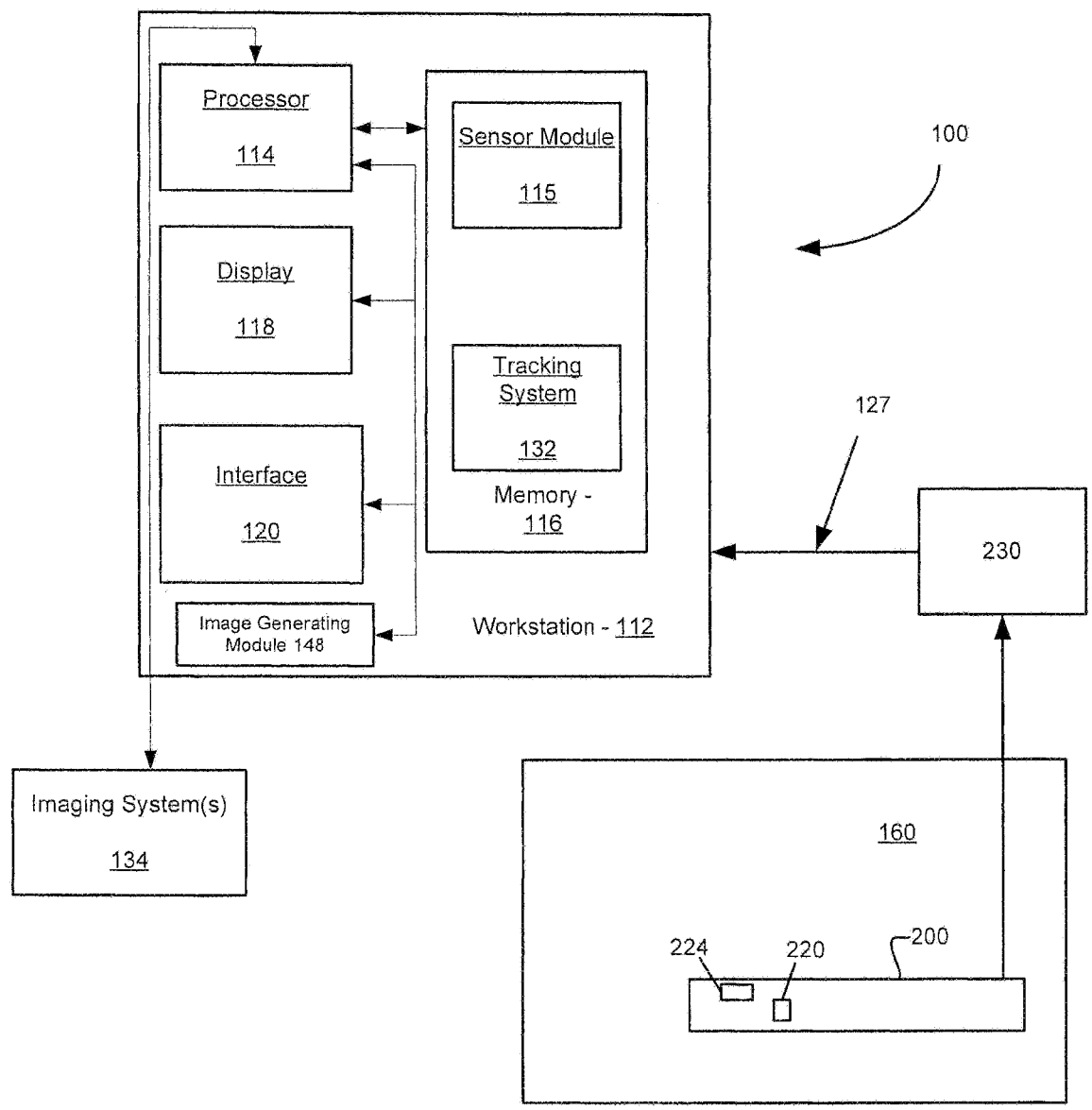
FIG. 1 is system for tracking a medical device embodying present principles.

A system, medical device and method will hereinafter be described that embodies present principles. The medical device is configured to deploy a medical instrument lateral to a central axis of the device. The device includes electromagnetic sensors that create a virtual axis in alignment with an opening in the device that is positioned off of the central axis of the device. Further described in accordance with present principles are a system and method that employ the medical device. In another embodiment, the system embodying the present principles provides for tracking the medical device within a patient's body, and the locating of the virtual axis and the adjustment of same. In another embodiment, the method provides for conducting a procedure that employs the medical device and system.

The medical device has a distal portion provided with an opening positioned lateral to the central axis of the device to allow for a tool or instrument to be deployed laterally, e.g., lateral to the central axis of the device. The device includes electromagnetic sensors in the form of a plurality of wound coils of an electromagnetic material that are positioned relative to each other as described herein that allows for the virtual axis of instrument deployment to be tracked. The virtual axis, which passes through the opening positioned in a side of the device, is not aligned with the central axis of the device, e.g., an axis defined by the longitudinal direction of the device. In one embodiment, the virtual axis and the central device axis intersect with each other at an angle, e.g., an oblique angle.

A current source, e.g., an AC current source, is connected to at least one of the coils for generating a magnetic field. Magnetic fields are generated that are believed to be responsible for generating the virtual axis. The coil configuration in the aforementioned alignment generates magnetic fields that correspond to the virtual axis extending through the laterally positioned opening in the side of the device.

In one embodiment, the electromechanical sensors are a pair of wound coils fabricated from an electromagnetically conductive material. One coil is a first coil that fits within the device at a distal portion thereof and is aligned along the longitudinally-extending central axis of the device. In one embodiment, the first coil is concentric with the central axis of the device. The second coil is positioned near to the first coil and is aligned orthogonally with respect to the first coil. In one embodiment, the second coil is positioned to a side of the central axis of the device, e.g., lateral to the central axis. The second coil may be positioned to the side of a central device lumen that is aligned with the central axis.

Prior to describing the particular embodiments, it is understood that the functions of the various modules, elements, and components shown in the figures can be provided through the use of dedicated hardware (e.g., individual circuits or integrated circuitry) as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present principles can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, depicted is a system 100 for tracking a medical device having a virtual axis is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store a sensor module 115. The sensor module 115 may be stored in memory 116 or be included as a separate unit. The sensor module interprets the position and orientation of the medical device 200, and is capable of registering coordinate systems of a device imaging system 134 and the tracking system 132. The sensor module 115 is configured to receive feedback from at least two systems, including the system embodying the sensor output readout-equipment 230, and additional systems that may also be employed. The sensor module 115 can transform one coordinate system to the other, transform the local coordinate systems to a common global coordinate system or employ intermediate or other coordinate systems, as the case may be.

The medical device 200 may include a bronchoscope, a catheter, a guidewire, a probe, an endoscope, or other medical component. Medical device 200 may be a device used in prostate interventions, a device used in endoscopic retrograde cholangiopancreatography (ERCP), and could be a robotic device that is tracked electromagnetically. In one embodiment, the medical device has a cannula sized and dimensioned to pass through a body passageway, the medical device having a central lumen for passing and transporting a medical instrument.

The electromagnetic sensors 220, 224 are coupled to the device and connect to the sensor output readout equipment 230, which connects to workstation 112 through wiring 127.

In one embodiment, workstation 112 includes an image generation module 148 configured to receive feedback from an optional shape sensing device (not shown) and record accumulated position data as to where the shape sensing device has been. An image of the shape sensing device generated by imaging system 134 can be displayed on a display device 118. Workstation 112 includes the display 118 for viewing internal images of a subject (patient) 160 and may include the image as an overlay or other rendering of the history of previous positions of the device. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The tracking system 132 includes an electromagnetic (EM) tracking system that includes electromagnetic sensing coils 220, 224, which track spatial positions of the device. The coils are connected as set forth above through to the workstation 112. Electrical signals are transported to and from the sensors. If necessary, the system may include one or more amplifiers (not shown) for strengthening the electrical output signal of the sensors. Other tracking systems may include optical tracking systems, optical shape sensing systems or any other suitable tracking system.

In one embodiment, workstation 112 records data as to where the device 200 is within the patient 160. Workstation 112 may include a display 118 for viewing internal images of patient 160 and may include ultrasound images as an overlay or other rendering which also shows the device 130 and its positions. Display 118 may also permit a user to interact with the workstation 112 and its components and functions, or any other element within the system 100. This is further facilitated by the interface 120.

Figure 2A:
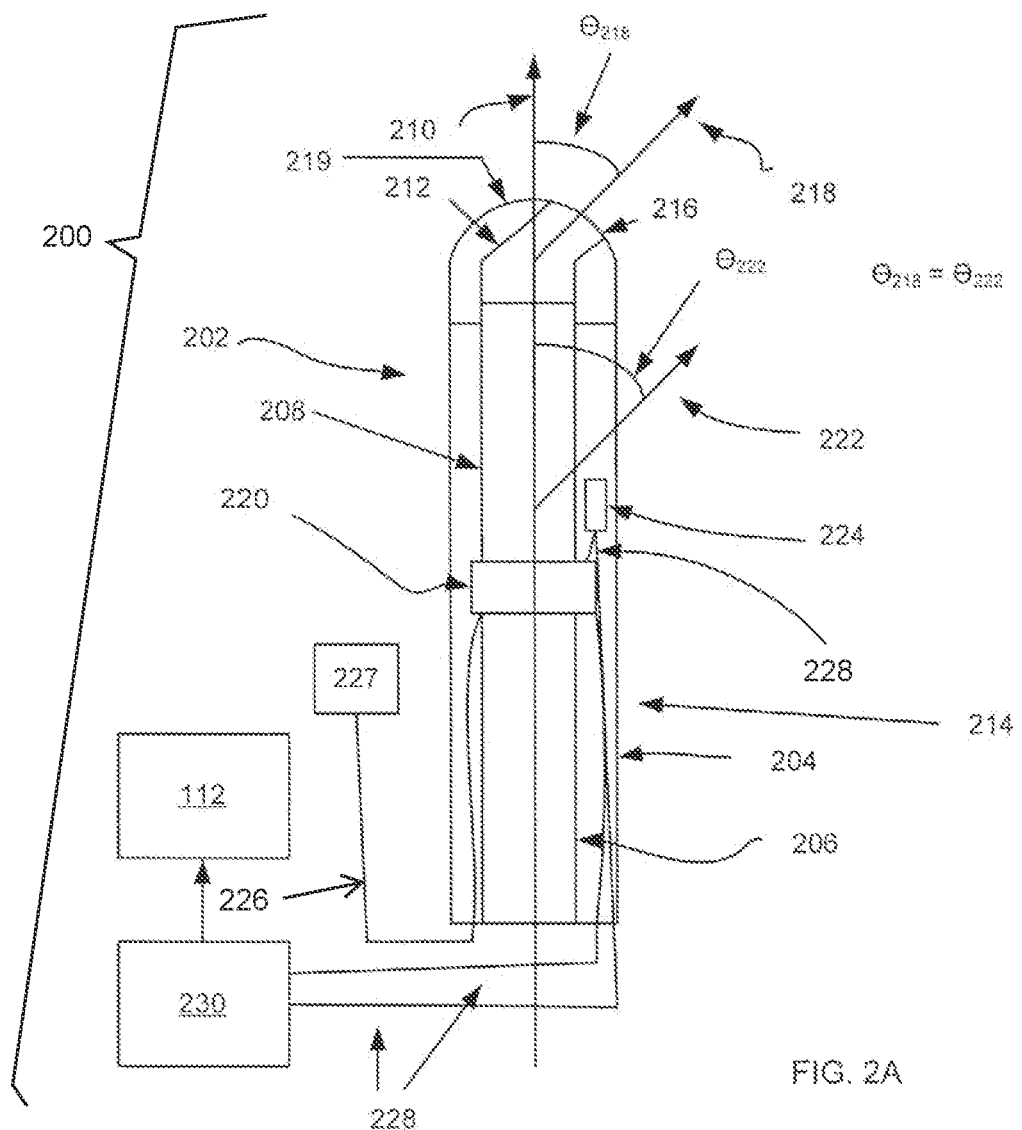
FIG. 2A depicts a cross sectional view of a distal portion of medical device in accordance with present principles.

Referring to FIG. 2A, depicted is a medical device 200, at the distal portion 202 of medical device 200. Medical device 200 has an outer cannula 204 provided with central lumen 206 through which a medical instrument, e.g., a biopsy needle (not shown) can be guided. The cannula 204 is designed to have a diameter/cross sectional profile that would allow the device to fit in and travel through a body passageway of the patient, e.g., the air pathways in the lungs of a mammal, such as a human. The central lumen 206 has a portion 208 that is concentric along the central axis 210 of the medical device 200. The central lumen 206 includes a turn 212 that gradually turns the central lumen laterally, i.e., towards sidewall 214 of the device. The turn communicates with opening 216 in the tip 219 of the device. The opening 216 is positioned laterally to the central axis of the device. Tool insertion axis 218 is defined through the turn 212 and laterally positioned opening 216 of the medical device 200.

Device 200 further includes coil 220 positioned along the central axis 210 of the device and affixed thereto. Coil 220 is aligned with the central device axis 210 is concentric with the central device axis.

Second coil 224 is positioned near to and in orthogonal alignment with the first coil 220 and is affixed to the device. As depicted, the central axis of second coil is at a right angle to the central axis of the first coil 220. The central axis of second coil is perpendicular to the central axis of the first coil 220. The central axes of the first and second coils are the axes that pass through the hollow middle of the coils, which in one embodiment, are coreless coils.

In one embodiment, the second coil 224 is positioned to the side of the central axis 210 of the device, and to the side of the central axial portion 208 of the central lumen 206 of the device.

In an embodiment, first coil 220 is larger than the second coil 224. In one embodiment, this is due to a difference in the number of wire windings of the first and second coils, with the number or wire windings respectively expressed as $N_1$ and $N_2$, where N is the number of turns, the subscripts identify the first and second coils respectively, and $N_1 > N_2$. FIG. 2B depicts first coil having $N_1$ turns. FIG. 2B is intended to be exemplary; the same configuration could apply to second coil 224.

The first coil 220 and the second coil 224 are wound from an electromagnetic material having a predetermined number of turns $N_1$ and $N_2$ and coil cross sectional area $A_1$ for the first coil 220 and $A_2$ for the second coil 224. FIG. 2C depicts first coil cross sectional area $A_1$. FIG. 2C is intended to be exemplary; the same configuration could apply to second coil 224.

The multiplication product of N·A provides a sensitivity value S employed to align the tracker vector 222 with the tool insertion axis 218 that passes through laterally positioned opening 216 of the device. With this arrangement, the tracker vector 222, also referred to herein as the virtual axis, is aligned with the device opening 216. This arrangement can effectively track a medical instrument traveling along the tool insertion axis 218 passing through the device opening 216, since the virtual axis 222 and the tool insertion axis 218 are aligned with each other.

In the exemplified arrangement, the electromagnetic coils 220, 224, when generating magnetic effects due to electrical excitement, will provide a signal that is a weighted average of the two coils that aligns along the virtual axis. By coordinating the sensitivity $S_1$ of the first coil and second coil $S_2$ to arrive at the virtual axis, a sensor arrangement could fit into the space allowed by existing device designs while providing for direct tracking of the tool insertion pathway along the virtual axis.

Figure 3:
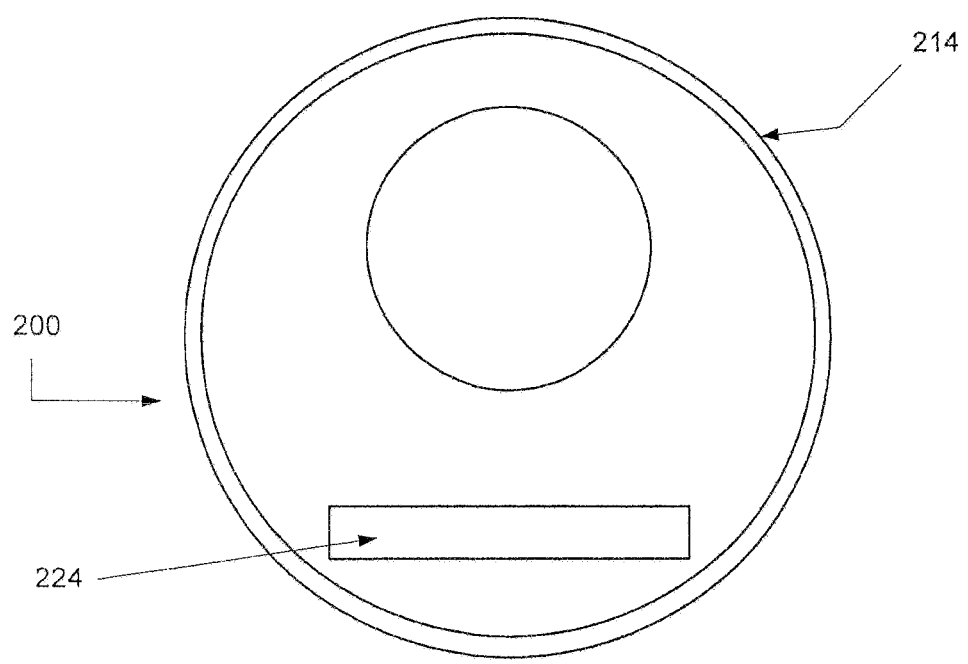
FIG. 3 depicts a top plan view of a device design with a lateral opening.

FIG. 3 shows an inventive arrangement in which the second coil 224 fits within the cross sectional geometry of the lumen along with a medical instrument, e.g., needle (not shown) that travels though the device to a site of a medical procedure and thereby provides an arrangement for tracking an instrument as it deploys laterally through the opening in the device.

Referring to FIG. 2A, it is shown that the tracker vector angle $\theta_{222}$ generated by the sensor arrangement is the same as the tool insertion axis angle $\theta_{218}$, as the generated virtual axis is aligned with and passes through the device opening 216. Further shown is the electrical wiring (input and output) 226, 228 connecting an AC current 227 source to the tracking arrangement and to a measuring instrument 230. In one embodiment, the coils are wired in series.

Information from the sensors is analyzed by sensor output readout-equipment 230 which is exemplified by a synchronous voltage (amplitude+phase) detector. The excitation source could be a current source(s) with a suitable frequency and phase profile(s) applied to one or more coils. A synchronous voltage detector resolves the measured signal against the excitation and thereby a determination concerning the geometrical relation between the coil components can be made. In another embodiment, an AC voltmeter is used in the analysis. In one embodiment, the electrical sensor output signal is amplified with a suitable amplifier (not shown).

Embodying one embodiment of present principles, at least one of the first coil 220 and the second coil 224 are cylindrically symmetrical. In one other embodiment, all provided coils are in this arrangement. In one other embodiment, the at least one coil is a unit of helically wound loops, which loops define circular areas, the at least one coil thus being cylindrically symmetrical. In one other embodiment, all provided coils are in this arrangement. In one other embodiment of present principles, the loops of the at least one coil define areas that are substantially perpendicular to a lengthwise axis X that passes through the coil. In one other embodiment, all provided coils are in this arrangement. Lengthwise axis X is shown in FIG. 2C centered in the coil in an example that employs first coil 220, which arrangement could also apply to second coil 224. Lengthwise axis X passes through the coil, i.e., it passes through the drawing page. In another aspect, the first coil and the second coil both meet at least one of the criteria of this paragraph.

Figure 4:
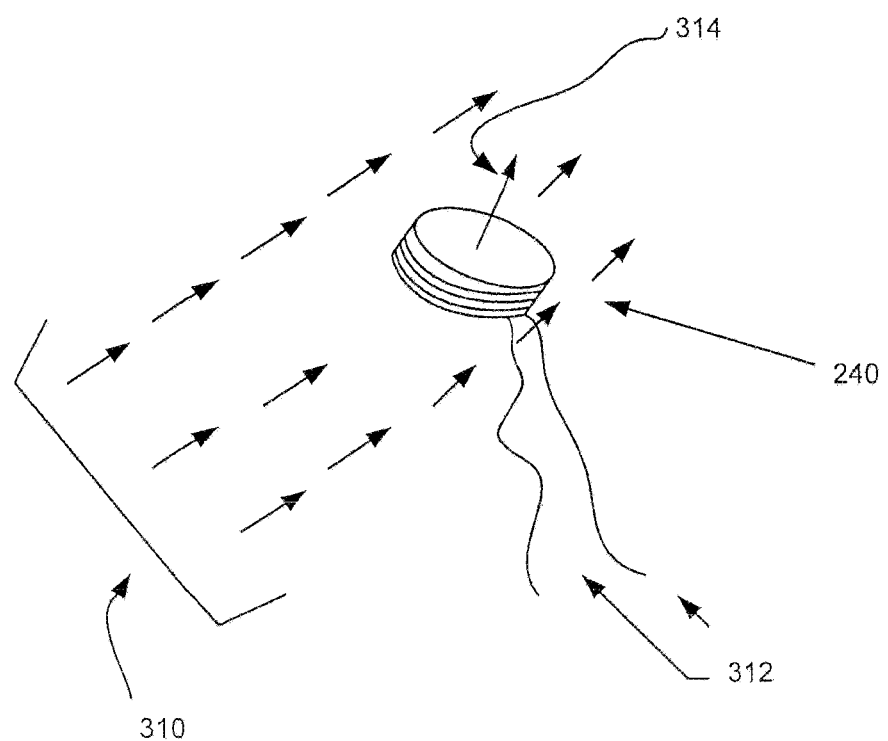
FIG. 4 depicts an electromotive force (EMF) induced on a coil in a time-varying magnetic field.

Electromagnetic tracking employed in the present application relies upon electromagnetic induction. An alternating current in a primary coil generates a time-varying magnetic field. A pickup coil having a number of turns N and a cross-sectional area A placed in the field of influence of the primary coil will experience an induced electromotive force (EMF). This is illustrated in FIG. 4 in which EMF is induced in an electrically exited coil 240 with leads 312 in a time-varying magnetic field, with 310 showing the magnetic flux density B. Coil 240 has a sensitivity S that is reflective of the ability to encircle magnetic lines of flux proportional to the dot product of the number of coil windings N and the cross-sectional area A encircled by the coil. Further, the sensitivity has effective direction 314 that extends normal to the encircled coil area 240, pointing in a right-hand-sense when considering the coil-winding. Sensitivity and its effective direction (vector) is dependent on coil positioning and orientation, number of wire turns N, and cross-sectional areas A of the coils. The EMF generated by this coil is the dot product of the sensitivity and the ambient rate of change of flux density. In a formula, $EMF_{240} = N \cdot \overline{A} \cdot dB/dt$.

The EMF generated per rate of change of flux density by a given pickup coil is dependent in part on the sensitivity of the pickup coil in its particular position and orientation as referenced to the primary source of the generated magnetic field. Connecting two coils in series, as may be the case in described embodiments, the EMF resulting from the combination corresponds to the tracker vector 222 (FIG. 2A). The resulting EMF is a vector-sum of the individual sensitivities. The two coils can each be advantageously wound in the aforedescribed directions for the first coil 220 and the second coil 224.

From this the vector of the combination "virtual" coil is aligned with, e.g., is parallel to the tool insertion axis passing through the opening in the side of the device. As shown, the tracker vector 222 aligns with the tool insertion axis 218 along angle θ (FIG. 2A). This is the product of adjusting the sensitivities of the two coils, in which they are coordinated to provide alignment and generate a virtual axis.

Figure 5:
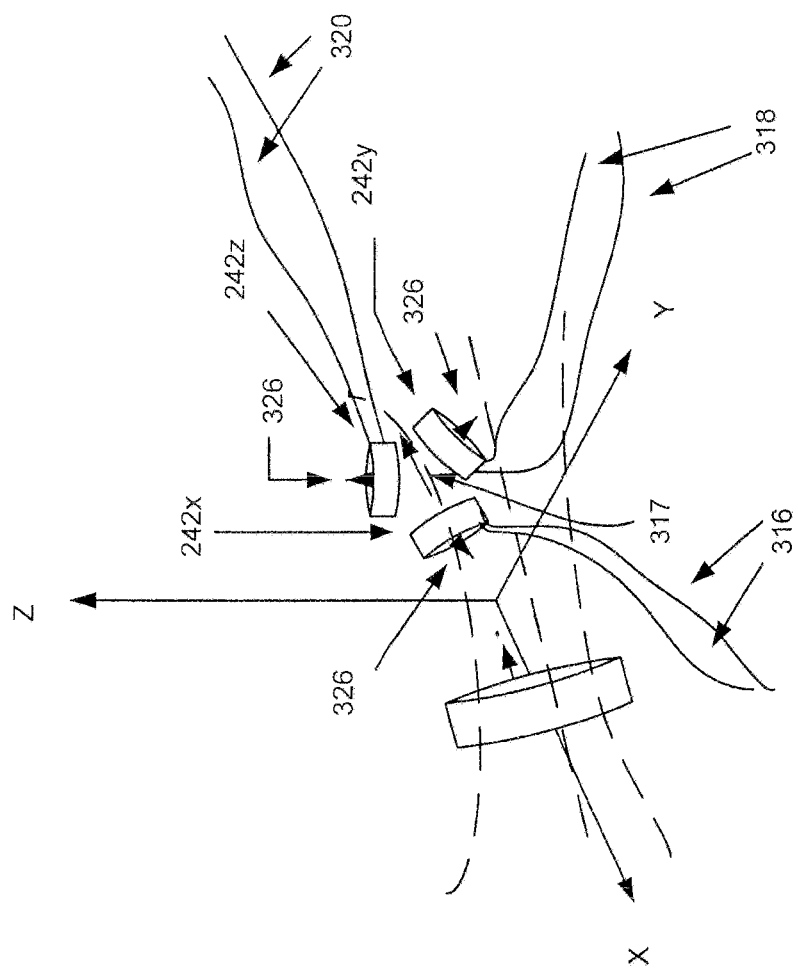
FIG. 5 depicts a magnetic field resolved along Cartesian coordinate-axes.

Referring to FIG. 5, when the magnetizing source—which can be a primary coil 242 subjected to a magnetizing current—generates the time-varying field, the flux density at a point in a given coordinate frame of reference can be resolved into its coordinate components. The flux density B at a certain point is shown resolved in the three axes of a Cartesian coordinate system. Three pickup coils 242x, 242y, 242z, which are orthogonal to each other, are respectively aligned with the x, y, z axes, and which are respectively coupled to electrical wires 316, 318, 320, represent the components of the varying magnetic flux density B, denoted 317, in terms of three EMF directions Ux, Uy and Uz of the relatively large coil 242 spatially arranged in the x, y and z planes. Observing the x, y and z component EMFs, it is possible to determine the rate of change of flux (vector) at that point. In formulas, the magnetic flux density $B = B_x + B_y + B_z$; the EMF U for the x, y, z components, as exemplified by coil 242z is $U_{242z} = N \cdot \overline{A} \cdot dB_{242z}/dt$. Leads 316, 318, 320 are coupled to a device for analyzing the EMF components Ux, Uy and Uz. Note that the effective sensitivity 326 has x, y and z components.

In one arrangement, the rate of change of the (vector) flux-density may be measured and resolved along orthogonal axes through the generated EMFs. Conversely, superposition may be applied, whereby the addition of two EMFs from two separate (e.g. orthogonal) pickup-coils may be used to emulate the EMF on a single pickup coil corresponding to the sum of the two coils. See FIG. 6, in which superposition of coils 244, 246 (EMF Ua) is used to create an equivalence of a combination to a single pickup-coil 245 (EMF Ub), where Ua≈Ub. Electrical wires 322, 324 are coupled to a device for analyzing the EMF components Ua, Ub. Note that the effective sensitivity 328 has x, y and z components.

An approximation of the EMF caused by a time varying flux density on a pickup coil at a given point may be obtained by combining two separate coils 248, 250 (EMF Ua), each placed away from the particular point. This is illustrated in FIG. 7. A single pickup coil 252 (EMF Ub) may be approximated by a sum of multiple parallel coils 248, 250 (EMF Ua), which are connected in series by wire 321. Here, Ua≈Ub. Electrical wires 330, 332 are coupled to a device for powering coils and analyzing the EMF components Ua.

The combination of multiple coils can be regarded as a virtual coil, the sensitivity of which is a vector sum of the sensitivities of each of its constituent coils. As described in accordance with present principles, two orthogonal coils can be used to create a virtual coil on an axis that is tilted with respect to the central device axis. For a device described in FIG. 2A with a side opening 216 that tracker vector 222 passes through, such as a biopsy sampling medical device, a virtual, inclined coil is realized by combining the vectors of the first and second electromagnetic sensing coils 220, 224 to create the virtual tracking axis, e.g., tracker vector 222. Other arrangements as described herein are also possible.

Figure 8A:
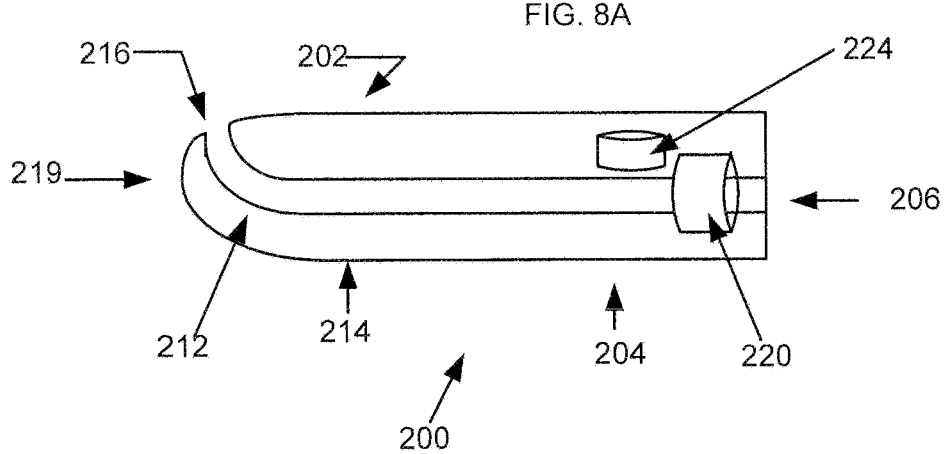
FIGS. 8A and 8B are cross-sectional views depicting a distal portion of a medical device according to the present principles.
Figure 8B:
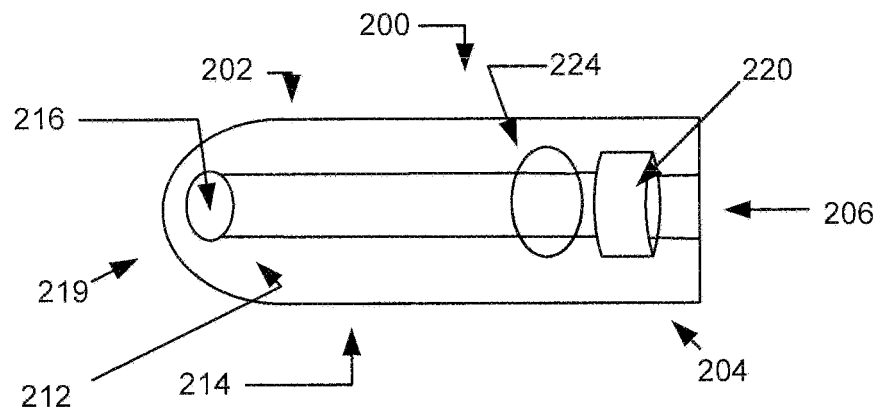

Referring to FIGS. 8A and 8B, parts numbers are the same as indicated with regard to FIG. 2A. FIGS. 8A, 8B show the second coil 224 in orthogonal arrangement with respect to first coil 220. Second coil 224 is positioned to the side of the concentric portion 208 of the central device lumen 206, which lies concentric to the central device axis 210. First coil is concentric with the central device axis 210. The central device lumen 206 passes through the first coil 224 and is in concentric relationship with the first coil. Referring to FIG. 8B, turn 212 is shown as being a gradually rounded turn that communicates with opening 216.

In one embodiment, information from the sensors is analyzed by readout-equipment that could be a synchronous voltage (amplitude+phase) detector. The excitation source could be a current source(s) with a suitable frequency and phase profile(s) applied to one or more coil. A synchronous detector would resolve the measured signal against the excitation and thereby would draw conclusions about the geometrical relation between the coil components. In another embodiment, an AC voltmeter is used in the analysis.

FIG. 9 shows another inventive embodiment that is a method 800 for tracking a medical instrument coupled to a medical device in which the medical instrument is deployed along a tool insertion axis that is not aligned with a central device axis. The method contemplates employing the medical device 200 and system 100, but is not limited to them.

In block 810, a medical device with virtual axis tracking capability e.g., a plurality of coordinated electromagnetic sensors, is inserted into a patient for purposes of conducting a medical procedure in a location that that is not aligned with the central axis of the medical device. For example, the site of the medical procedure may lie outside of a body passageway that the medical device travels through.

The medical device is moved through a body passageway to a location where a medical procedure is to be conducted. In one embodiment, imaging systems such as ultrasound may be employed to position the medical device in the desired location.

In block 820, signals obtained from the electromagnetic sensors determine the location and positioning of the tracker vector, e.g., virtual axis, which is in alignment with the opening in the side of the medical device. This information determines if the virtual axis is aligned with the site of the medical procedure. If the virtual axis is in alignment, then the tool insertion axis through the device opening is in alignment with the site. For example, a tissue sample may be desired from a body location located at point A having, e.g., x, y and z coordinates in an exemplary three-dimensional configuration. The opening, and hence the tool insertion axis, should align with point A to order to obtain a tissue sample at the desired location. The information concerning tracker vector position (virtual axis) and direction obtained from the electromagnetic sensor, as translated by the system, informs a medical worker at the workstation whether the device is in proper position or whether adjustments should be made. For example, the medical device may have to be rotated about the central device axis to place the opening (and tool insertion axis) into alignment with the site for sampling.

In block 830, when it is determined that the location and position of the virtual axis are suitable for conducting the medical procedure, the medical instrument is inserted and moved through the device. In block 840, the medical instrument is directed through the opening in the device that is along the virtual axis. As a result, the medical instrument is aligned with the virtual axis. In block 850, the medical procedure is conducted at a lateral site, e.g., on a side of the body passageway or at a site outside of the body passageway. In any event, the medical device is directed to the site of the medical procedure and the medical procedure is conducted. After completion of the medical procedure, the medical instrument is retrieved in block 860, i.e., drawn back into the device, and the device is removed from the patient's body in block 870.

One specific embodiment employing the general principles described above is a bronchoscopy procedure in which a biopsy needle (instrument) is passed through a bronchoscope (instrument). The distal tip of the bronchoscope is provided with an opening not lying on the central axis of the scope, or in other words, the opening is lateral to the central axis of the device. The sample to be taken lies outside of the air passageway of the patient through which the bronchoscope will travel.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

"Comprising" does not exclude other elements or steps. "A" or "an" does not exclude a plurality. A single processor or other unit may fulfill the functions of several means recited in the claims.

Having described preferred embodiments of a virtually-oriented electromagnetic tracking coil for catheter based navigation, it is stated that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for tracking a medical instrument, the system comprising:
   a medical device configured to be inserted into a body, the medical device comprising:
      a plurality of coordinated electromagnetic sensors configured to generate a virtual axis of travel for the medical instrument along a channel of the medical device through an opening of the medical device, the virtual axis of travel aligned with a tool insertion axis, wherein structure of each of the plurality of coordinated electromagnetic sensors and position of each of the plurality of coordinated electromagnetic sensors on the medical device are coordinated to generate a vector-sum of individual sensitivities of the plurality of the coordinated electromagnetic sensors that aligns with the tool insertion axis,
      wherein the plurality of coordinated electromagnetic sensors comprises a first coil and a second coil, the first coil in concentric arrangement with a longitudinally-extending central axis of the medical device and the second coil in orthogonal arrangement to the first coil, the first coil and the second coil electrically connected in series; and
   a tracking circuitry configured to track the plurality of coordinated electromagnetic sensors to determine a virtual axis position of the medical instrument along the generated virtual axis of travel in a tracking space.

2. The system of claim 1, wherein the tracking circuitry includes a synchronous voltage detector.

3. The system of claim 1, further comprising a visual imaging system.

4. The system of claim 1, wherein the tracking circuitry includes an alternating current (AC) voltmeter.

5. The system of claim 1, wherein the opening is not aligned with the central axis of the medical device.

6. The system of claim 1, wherein the tracking circuitry is configured to generate the virtual axis relative to a position of the plurality of coordinated electromagnetic sensors.

7. The system of claim 1, wherein the first coil and the second coil are of an electromagnetic material and are positioned relative to each other in such a manner to enable generation of the virtual axis of travel for the medical instrument by the tracking circuitry.

8. The system of claim 1, wherein at least one of the first coil and the second coil is cylindrically symmetrical.

9. The system of claim 1, wherein the first coil and the second coil are cylindrically symmetrical.

10. The system of claim 1, wherein the first coil and the second coil are comprised of loops of wire windings, the loops of at least one of the first coil and the second coil defining an area that is substantially perpendicular to a lengthwise axis that passes through the at least one of the first coil and the second coil.

11. The system of claim 1, wherein the first coil and the second coil are comprised of loops of wire windings of respectively $N_1$ and $N_2$ turns, where N is the number of turns,
   the first coil and the second coil having respectively $A_1$ and $A_2$ cross sectional areas, wherein coil sensitivity values of respectively $S_1$ and $S_2$ are the multiplication product of N·A for each respective coil, and wherein $N_1 > N_2$.

12. The system of claim 1, wherein the first coil is concentric to the channel and the second coil is positioned to a side of the channel.

13. The system of claim 1, wherein the plurality of coordinated electromagnetic sensors are comprised of the first coil, the second coil, and a third coil respectively arranged along x, y, and z axes.

14. The system of claim 1, wherein the tracking circuitry is configured to apply an alternating current to the plurality of coordinated electromagnetic sensors in order to generate a time-varying magnetic field extending along and aligned with the tool insertion axis.

15. The system of claim 14, wherein the tracking circuitry is configured to track the medical instrument along the virtual axis based on an electromotive force that is induced in a pickup coil arranged on the medical instrument.

* * * * *